(12) United States Patent
Dekker

(10) Patent No.: US 6,805,673 B2
(45) Date of Patent: Oct. 19, 2004

(54) MONITORING MAYER WAVE EFFECTS BASED ON A PHOTOPLETHYSMOGRAPHIC SIGNAL

(75) Inventor: Andreas Lubbertus Aloysius Johannes Dekker, Maastricht (NL)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 10/081,887

(22) Filed: Feb. 22, 2002

(65) Prior Publication Data

US 2003/0163034 A1 Aug. 28, 2003

(51) Int. Cl.[7] ................................ A61B 5/08
(52) U.S. Cl. .......................... 600/529; 600/324
(58) Field of Search .................... 600/309–310, 600/322, 324, 507, 500, 529, 323, 325, 330

(56) References Cited

U.S. PATENT DOCUMENTS

| | | | |
|---|---|---|---|
| 3,704,706 A | 12/1972 | Herczfeld et al. | |
| 4,306,567 A | 12/1981 | Krasner | |
| 4,379,460 A | 4/1983 | Judell | |
| 4,404,974 A | 9/1983 | Titus | |
| 4,510,944 A | 4/1985 | Porges | |
| 4,765,340 A | 8/1988 | Sakai et al. | |
| 4,777,960 A | 10/1988 | Berger et al. | |
| 4,781,201 A | 11/1988 | Wright et al. | |
| 4,813,427 A | * 3/1989 | Schlaefke et al. | 600/484 |
| 4,858,638 A | 8/1989 | Cseri | 137/115 |
| 4,860,759 A | 8/1989 | Kahn et al. | |
| 4,863,265 A | 9/1989 | Flower et al. | 356/41 |
| 4,869,254 A | 9/1989 | Stone et al. | |
| 4,884,578 A | 12/1989 | Morgenstern | |
| 4,899,760 A | 2/1990 | Jaeb et al. | |
| 4,930,517 A | 6/1990 | Cohen et al. | |
| 4,958,638 A | 9/1990 | Sharpe et al. | |
| 4,960,129 A | 10/1990 | DePaola et al. | |
| 4,972,842 A | 11/1990 | Korten et al. | |
| 5,033,472 A | 7/1991 | Sato et al. | |
| 5,078,136 A | 1/1992 | Stone et al. | |
| 5,111,817 A | 5/1992 | Clark et al. | |
| 5,170,794 A | 12/1992 | Reiche | |
| 5,273,036 A | 12/1993 | Kronberg et al. | |
| 5,368,224 A | 11/1994 | Richardson et al. | |
| 5,385,144 A | 1/1995 | Yamanishi et al. | |
| 5,396,893 A | 3/1995 | Oberg et al. | |
| 5,423,322 A | 6/1995 | Clark et al. | |
| 5,431,159 A | 7/1995 | Baker et al. | |
| 5,482,036 A | 1/1996 | Diab et al. | |

(List continued on next page.)

OTHER PUBLICATIONS

Spectral Analysis: Review "Heart Rate Variability", Lukas Spieker, hemodynamics.ucdavis.edu, Unknown Publication Date.

Primary Examiner—Mary Beth Jones
Assistant Examiner—Matthew Kremer
(74) Attorney, Agent, or Firm—Marsh Fischmann & Breyfogle LLP

(57) ABSTRACT

A photoplethysmographic instrument is used to obtain physiological parameter information related to low frequency heart rate and blood volume variability. In one implementation, a plethysmographic signal is filtered relative to a Mayer Wave frequency to provide an output related to low frequency blood volume variability. In another implementation, the photoplethysmographic signal is first processed to obtain a heart rate signal and the heart rate signal is in turn processed to obtain information regarding low frequency heart rate variability. In either case, a Mayer Wave effect having potential diagnostic significance can be monitored using a photoplethysmographic instrument such as a pulse oximeter.

8 Claims, 16 Drawing Sheets

U.S. PATENT DOCUMENTS

| | | | | |
|---|---|---|---|---|
| 5,490,505 | A | 2/1996 | Diab et al. | |
| 5,511,553 | A | 4/1996 | Segalowitz | |
| 5,553,615 | A | 9/1996 | Carim et al. | |
| 5,555,882 | A | 9/1996 | Richardson et al. | |
| 5,575,284 | A | 11/1996 | Athan et al. | |
| 5,623,933 | A | 4/1997 | Amano et al. | |
| 5,755,229 | A | 5/1998 | Amano et al. | |
| 5,766,127 | A | 6/1998 | Pologe et al. | 600/310 |
| 5,776,071 | A | 7/1998 | Inukai et al. | 600/493 |
| 5,830,137 | A | 11/1998 | Scharf | 600/323 |
| 5,842,979 | A | 12/1998 | Jarman | 600/322 |
| 5,853,364 | A | 12/1998 | Baker, Jr. et al. | 600/300 |
| 5,862,805 | A | 1/1999 | Nitzan | |
| 5,865,167 | A | 2/1999 | Godik | |
| 5,865,756 | A | 2/1999 | Peel, III | 600/490 |
| 5,885,213 | A | 3/1999 | Richardson et al. | 600/336 |
| 5,902,235 | A | 5/1999 | Lewis et al. | 600/323 |
| 5,919,134 | A | 7/1999 | Diab | 600/323 |
| 5,931,779 | A | 8/1999 | Arakaki et al. | 600/310 |
| 5,934,277 | A | 8/1999 | Mortz | |
| 5,954,644 | A | 9/1999 | Dettling et al. | 600/322 |
| 5,971,930 | A | 10/1999 | Elghazzawi | 600/483 |
| 5,980,463 | A | 11/1999 | Brockway et al. | |
| 5,993,893 | A | 11/1999 | Kikuchi | 427/8 |
| 5,997,482 | A | 12/1999 | Vaschillo et al. | 600/484 |
| 6,011,985 | A | 1/2000 | Athan et al. | 600/322 |
| 6,027,455 | A * | 2/2000 | Inukai et al. | 600/490 |
| 6,028,311 | A | 2/2000 | Sodickson et al. | 250/343 |
| 6,064,910 | A | 5/2000 | Andersson et al. | 607/20 |
| 6,067,462 | A | 5/2000 | Diab et al. | 600/310 |
| 6,081,742 | A | 6/2000 | Amano et al. | 600/513 |
| 6,099,481 | A * | 8/2000 | Daniels et al. | 600/538 |
| 6,129,675 | A | 10/2000 | Jay | 600/485 |
| 6,155,992 | A | 12/2000 | Henning et al. | 600/583 |
| 6,358,201 | B1 * | 3/2002 | Childre et al. | 600/300 |
| 6,480,733 | B1 * | 11/2002 | Turcott | 600/516 |
| 6,519,486 | B1 * | 2/2003 | Edgar et al. | 600/323 |

* cited by examiner

MONITORING MAYER WAVE EFFECTS BASED ON A PHOTOPLETHYSMOGRAPHIC SIGNAL

FIELD OF THE INVENTION

The present invention relates, in general, to the noninvasive monitoring of low frequency heart rate and blood volume variability based on optical (visible and/or non-visible spectrum) signals and, in particular, to monitoring related parameters based on the processing of received optical signals. The invention can be readily implemented in connection with pulse oximetry instruments so as to expand the utility of such instruments.

BACKGROUND OF THE INVENTION

Photoplethysmography relates to the use of optical signals transmitted through or reflected by a patient's blood, e.g., arterial blood and/or perfused tissue, for monitoring a physiological parameter of the patient. Such monitoring is possible because the optical signal is modulated by interaction with the patient's blood. That is, interaction with the patient's blood, generally involving a wavelength and/or time dependent attenuation due to absorption, reflection and/or diffusion, imparts characteristics to the transmitted signal that can be analyzed to yield information regarding the physiological parameter of interest. Such monitoring of patients is highly desirable because it is noninvasive, typically yields substantially instantaneous and accurate results, and utilizes minimal medical resources, thereby proving to be cost effective.

A common type of photoplethysmographic instrument is the pulse oximeter. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, through the patient's appendage. The transmitted signals are received by a detector that provides an analog electrical output signal representative of the received optical signals. By processing the electrical signal and analyzing signal values for each of the wavelengths at different portions of a patient's pulse cycle, information can be obtained regarding blood oxygen saturation.

The algorithms for determining blood oxygen saturation related values are normally implemented in a digital processing unit. Accordingly, one or more analog to digital (A/D) converters are generally interposed between the detector and the digital processing unit. Depending on the specific system architecture employed, a single multi-channel digital signal may be received by the digital processing unit or separate digital signals for each channel may be received. In the former case, the digital processing unit may be used to separate the received signal into separate channel components. Thus, in either case, the digital processing unit processes digital information representing each of the channels. Such information, whether in digital or another form, defines input photoplethysmographic signals or "pleths."

These pleths generally contain two components. The first component is a low frequency or substantially invariant component in relation to the time increments considered for blood oxygen saturation calculations, sometimes termed the "DC component," which generally corresponds to the attenuation related to the non-pulsatile volume of the perfused tissue and other matter that affects the transmitted plethysmographic signal. The second component, sometimes termed the "AC component," generally corresponds to the change in attenuation due to the pulsation of the blood. In general, the AC component represents a varying waveform which corresponds in frequency to that of the heartbeat. In contrast, the DC component is a more steady baseline component, since the effective volume of the tissue under investigation varies little or at a low frequency if the variations caused by the pulsation of the heart are excluded from consideration.

Pulse oximeters typically provide as outputs blood oxygen saturation values and, sometimes, a heart rate and a graphical representation of a pulsatile waveform. The information for generating each of these outputs is generally obtained from the AC component of the pleth. In this regard, some pulse oximeters attempt to filter the DC component from the pleth, e.g., in order to provide a better digitized AC component waveform. Other pulse oximeters may measure and use the DC component, e.g., to normalize measured differential values obtained from the AC component or to provide measurements relevant to motion or other noise corrections. Generally, though, conventional pulse oximeters do not monitor variations in the DC component of a pleth or pleths to obtain physiological parameter information in addition to the outputs noted above.

SUMMARY OF THE INVENTION

The present invention is directed to using photoplethysmography to obtain physiological parameter information related to low frequency heart rate and blood volume variability. The invention thus provides important diagnostic or monitoring information noninvasively. Moreover, various aspects of the invention can be implemented using one or more channels and/or other components of a conventional pulse oximeter, thereby providing additional functionality to instruments that are widely available and trusted, as well as providing access to important information for treatment of patients on a cost-effective basis.

It has been recognized that low frequency heart rate and blood volume variability have important diagnostic significance and that such variability can be conveniently monitored through appropriate processing of pleth signals. In the latter regard, the pleth signal includes information regarding the patient's pulsatile waveform and can be processed to provide information regarding waveform variations. Spectral analysis of heart frequency indicates that such spectra characteristically include three peaks: a peak associated with respiration that typically has a frequency around 0.3 to 0.5 Hz, but may have a frequency of 1 Hz or greater in the case of infants; a peak typically in the 0.1 Hz range associated with the autonomic nervous system or vaso motor center, sometimes termed the "Mayer Wave"; and a very low frequency peak, e.g., less than 0.05 Hz, associated with temperature control. Regarding the second of these, the origin and nature of the Mayer Wave is not fully settled. For present purposes, the Mayer Wave relates to a low frequency variation in blood pressure, heart rate, and/or vaso constriction.

The Mayer Wave has particular significance for diagnostic and patient monitoring purposes. In particular, the amplitude and frequency of the Mayer Wave are seen to change in connection with hypertension, sudden cardiac death, ventricular tachycardia, coronary artery disease, myocardial infarction, heart failure, diabetes, and autonomic neuropathy and after heart transplantation. The present invention is based, in part, on the recognition that effects related to the Mayer Wave can be monitored based on analyzing a pleth to obtain physiological parameter information. In particular, it is expected that the Mayer Wave influences heart rate (and related parameters such as variations in blood pressure and blood volume) by direct influence on the vaso motor center. A pleth signal can be processed to monitor heart rate and variations therein, thus yielding diagnostic information related to the Mayer Wave. Alternatively or additionally, the pleth signal can be processed to monitor blood volume variations to obtain similar information related to the Mayer Wave.

A difficulty associated with obtaining physiological parameter information based on the Mayer Wave relates to distinguishing the effects associated with the Mayer Wave from effects associated with the above-noted respiration wave, particularly in view of the fact that each of these waves can occur within overlapping frequency ranges. There are a number of ways in which the Mayer Wave and the respiration wave can be distinguished, as described in detail in U.S. patent application Ser. No. 10/790,950, entitled "Monitoring Physiological Parameters Based on Variations in a Photoplethysmographic Signal", filed concurrently herewith. It has been recognized that the spectral composition or frequency band of the Mayer Wave can be readily characterized and the Mayer Wave can conveniently be analyzed, for purposes of monitoring related blood volume and heart rate variations, by controlling or having the patient control his respiration rate to be outside of the Mayer Wave frequency band under analysis.

Thus, in accordance with one aspect of the present invention, a method is provided for monitoring a Mayer Wave effect, such as a low frequency variation in blood pressure, heart rate, blood volume and/or vasoconstriction. The method involves obtaining a pleth signal that is modulated based on interaction of a transmitted optical signal with a patient's blood (e.g., arterial blood and/or perfused tissue), processing the pleth signal to identify an effect related to the Mayer Wave, and providing an output related to the Mayer Wave effect (e.g., a waveform, one or more values or other information, e.g., related to the amplitude and/or period/frequency of the Mayer Wave or variations therein). This method may be implemented in connection with a conventional pulse oximeter. In this regard, the step of obtaining a pleth signal may involve operating the pulse oximeter to transmit optical signals relative to the patient and provide a detector signal representative of the received optical signals and accessing at least a portion of the detector signal corresponding to one or more channels of the transmitted optical signals. For example, the oximeter may be operated to transmit single or multiple channel (e.g., red and infrared channels) signals. In either case, the detector signal will generally include a pleth signal. In the case of a multiple channel detector signal, each channel will generally include a pleth signal and information regarding one channel may be accessed in accordance with the present invention, or information regarding multiple channels may be used, e.g., by combining the channel signals.

Once the pleth is obtained, it may be processed in a variety of ways to identify a Mayer Wave effect of interest. In one implementation, such processing involves frequency based filtering to identify the effect of interest. In particular, a signal or series of values representing or otherwise based on the obtained pleth signal is filtered to selectively pass a spectral peak located between about 0.05 Hz and 0.5 Hz. The lower end of this range may be selected to eliminate at least a substantial portion of spectral power related to the very low frequency peak noted above associated with temperature control. The upper end of the noted range may be selected in conjunction with controlling the patient's respiration rate. In this regard, 0.5 Hz will allow for separation of the Mayer Wave from the respiration wave for many applications. A filtering range of between about 0.08–0.2 may be preferred for isolation of the Mayer Wave from the noted, potentially interfering spectral peaks. More preferably, because the Mayer Wave is generally found within a narrow frequency band at about 0.1 Hz, a narrow band pass filter may be utilized having a nominal pass band width (designated in conventional fashion) of no more than about 0.05 Hz and including within such pass band (preferably substantially centered relative thereto) or the frequency 0.1 Hz. Such filtering generally enables identifying a Mayer Wave effect from the signal under analysis.

In accordance with another aspect of the present invention, a low frequency blood volume variation of a patient is monitored. The associated method involves obtaining a pleth signal (e.g., as described above), processing the pleth signal to obtain information regarding a low frequency blood volume variation of the patient, and monitoring the low frequency blood volume variation over time to identify a characteristic of interest for patient monitoring or diagnostic purposes. The low frequency blood volume variation generally relates to a spectral peak of the pleth signal located between about 0.05 Hz and 0.5 Hz. Thus, the obtained pleth signal may be band pass filter, as discussed above, to extract information regarding the noted blood variability. Because such low frequency blood volume variability is related to the Mayer Wave, changes in its amplitude and/or frequency may have diagnostic significance as noted above.

In accordance with a further aspect of the present invention, a low frequency heart rate variability of a patient is monitored. The associated method involves obtaining a pleth signal, analyzing the pleth signal to obtain heart rate information, analyzing the heart rate information to obtain information regarding heart rate variability information, and monitoring the heart rate variability information to identify a characteristic of interest. The resulting heart rate variability information may be monitored, for example, to identify Mayer Wave phenomena of potential diagnostic significance.

The step of obtaining a pleth signal generally involves receiving a digital signal representative of an optical signal modulated based on interaction with perfused tissue of a patient. Such a signal may be provided using components of a conventional pulse oximeter. Pulse oximeters typically transmit red and infrared signals, thereby yielding red and infrared pleths. Either or both of these pleths may be utilized in accordance with the present invention. In particular, each of these pleths generally has a fundamental frequency corresponding to the patient's heart rate. Accordingly, either pleth can be used to yield the desired heart rate information. In general, for normally oxygenated patients, the infrared channel typically has the stronger pleth waveform and may be preferred for heart rate calculations. For poorly oxygenated patients, the red pleth may be preferred. In many cases, a combination of the two signals may provide a better waveform for heart rate analysis than either signal alone.

The pleth may be processed to obtain heart rate information in a variety of ways. As noted above, the pleth is generally a periodic signal having a fundamental frequency corresponding to the patient's heart rate. Accordingly, heart rate may be determined by performing peak-to-peak measurements on the pleth to determine the pulse period and, hence, pulse frequency. For example, such maxima may be obtained by identifying a change in sign of differential values between successive samples or groups of samples along the pleth or of a function fitted to the pleth. Alternatively, other points on the waveform, such as nominal zero (or average pleth value) crossings may be monitored. Such zero crossings would be expected to have a frequency of twice the heart rate. Such period measurements can be complicated due to the typically noisy waveform of the pleths. Accordingly, multiple waveforms may be utilized.

Additionally, the heart rate calculations may be performed in the frequency domain. In this regard, a processor may be configured to obtain a Fourier transform of the pleth. Once the Fourier transform is obtained, the pulse rate can be identified as the fundamental frequency of the pleth corresponding to the patient's heart rate. In any case, once the heart rate is determined, it can be monitored to identify low frequency variations of interest. In particular, oscillatory variations having a frequency associated with the Mayer Wave, as discussed above, may be monitored for diagnostic purposes.

One or more filters may be used in obtaining heart rate variability information based on a pleth signal in accordance with the present invention. In this regard, an adaptive filter may be used to track the fundamental frequency of the pleth and, hence, the patient's pulse rate. For example, such a filter may function as a narrow band pass filter having a band pass that is centered on the fundamental frequency of the pleth. The transfer function of the filter may be varied, e.g., based on analysis of successive waveforms, to track the potentially changing fundamental frequency. The filter or associated logic may thus be adapted to output a time series of pulse rate values. Such a time series of pulse rate values, whether obtained as an output of an adaptive filter system or otherwise, may be filtered using an adaptive filter that tracks a selected spectral peak of the time series to provide an output related thereto. Such filtering provides a fast, robust and computationally efficient mechanism for noninvasively monitoring low frequency heart rate variability based on pleth signals.

According to a still further aspect of the present invention, a method is provided for monitoring a patient using a pleth instrument. The method involves configuring a pleth instrument relative to the patient for a pleth analysis, e.g., by attaching a probe to the patient, causing a respiration rate of the patient to be at least at a given threshold, operating the instrument to obtain a pleth signal, and operating the instrument to process the pleth signal to identify an effect related to the Mayer Wave and provide an output related thereto. As noted above, the Mayer Wave generally has a frequency of about 0.1 Hz. Accordingly, the threshold is preferably greater than 0.1 Hz, for example, at least about 0.167 Hz or 10 breaths a minute. In this regard, the patient's respiration rate may be controlled, e.g., using a respirator, or the patient may be instructed to control his breathing. The pleth instrument may be operated to obtain a single or multi-channel pleth signal and one or more such channels may be processed to identify any suitable pleth effect such as low frequency variations in blood volume, pulse rate, blood pressure or vasoconstriction. Information relating to the effect of interest may be output as discussed above. Such use of a pleth instrument in conjunction with frequency controlled patient breathing allows for convenient monitoring of Mayer Wave effects.

An apparatus in accordance with the present invention includes an input port for receiving a pleth signal, a processor for processing the pleth signal to identify an effect related to the Mayer Wave and an output port for providing output information relating to the effect of interest. For example, the input port may be adapted for receiving a cable connected to a probe or may be a processor module configured to access a digital signal, and the output port may be a port configured to interface with an external monitor or other display device or may be a processor module configured to provide access to the output information in digital form. The processor preferably includes a filter for use in extracting information regarding the Mayer Wave effect directly from the pleth signal or from processed information obtained therefrom. For example, the pleth signal may be filtered to obtain low frequency blood volume variation information, or the pleth signal may be processed to provide heart rate information and this information may be filtered to yield low frequency heart rate variability information. The apparatus may be incorporated into a conventional pleth instrument such as a pulse oximeter. In this manner, the functionality of pulse oximeters may be advantageously extended.

BRIEF DESCRIPTION OF THE DRAWINGS

For a more complete understanding of the present invention and further advantages thereof, references now made to the following detailed description, taken in conjunction with the drawings, in which.

DETAILED DESCRIPTION

The present invention relates to obtaining physiological parameter information for a patient based on an analysis of a pleth signal involving identifying an effect associated with a Mayer Wave component of the pleth signal. In the following discussion, the invention is described in the context of an implementation utilizing components of a conventional pulse oximeter. The invention has particular advantages in this regard as such an implementation enhances the functionality of conventional pulse oximeters and provides important physiological parameter information in a cost effective manner. However, it will be appreciated that various aspects of the invention are not limited to such a pulse oximeter or other multi-channel signal implementations and the invention may be embodied in a dedicated single or multi-channel photoplethysmography instrument. Accordingly, the following discussion should be understood as exemplifying the invention and not by way of limitation.

Figure 1:
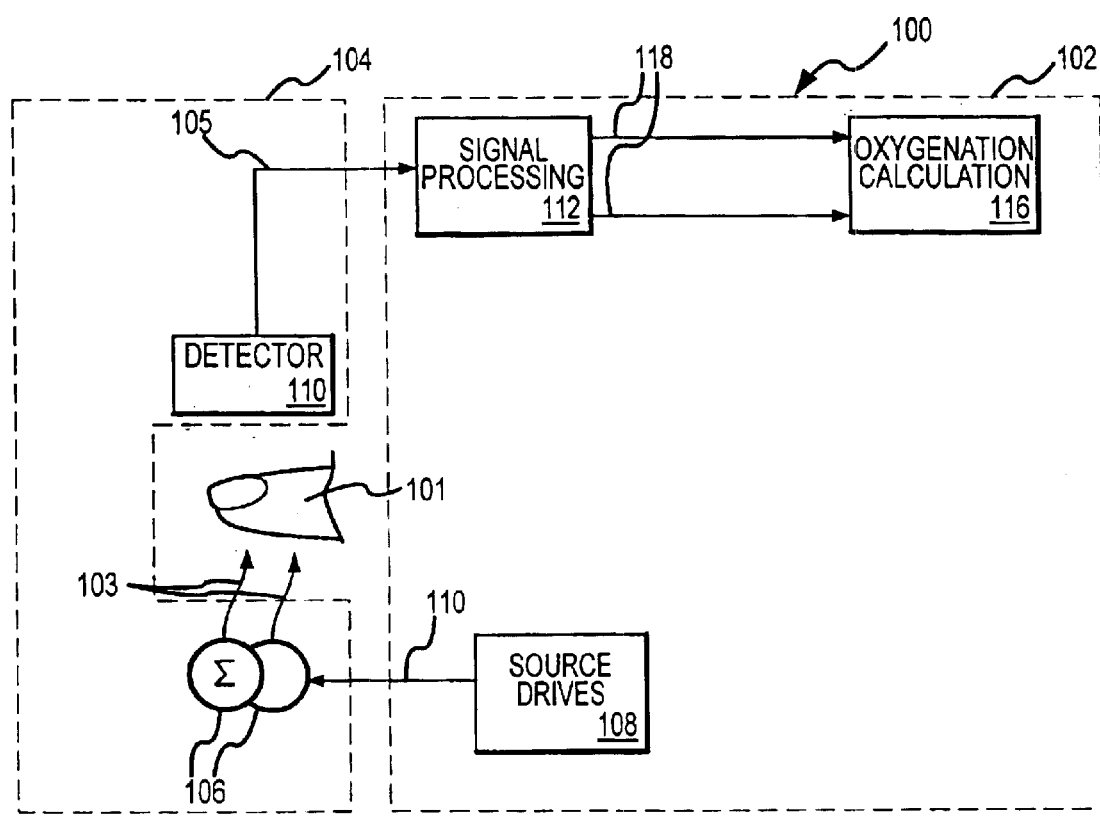
FIG. 1 is a schematic diagram of a pulse oximeter in accordance with the present invention.

Referring to FIG. 1, a schematic diagram of a pulse oximeter 100 in accordance with the present invention is shown. The oximeter 100 generally includes an instrument housing 102 and a probe 104 for attachment to a finger 101 or other appendage of a patient under analysis. In the illustrated embodiment, the probe 104 includes two or more sources 106 and a detector 110. It will be appreciated that either or both of these components may alternatively be located in the housing 102 and may be optically connected to the probe 104 by fiber optics or the like. Additionally, the sources 106 and/or detector 110 may be located in the cable or other coupling operatively between the probe 104 and the housing 102. The sources 106 are driven by source drives 108. The drives 108 serve to modulate the signals 103 in any of various ways. In this regard, the signals 103 transmitted by the sources 106 may be time division multiplexed, frequency division multiplexed, code division multiplexed, or the like. Such multiplexing facilitates separation of the signals from each of the channels during hardware or software based signal processing. The sources 106 provide two or more channels of signals 103. Each channel has a unique spectral content, e.g., wavelength or wavelength band. In the illustrated embodiment, two sources 106 are shown; one of the sources may have a red-centered wavelength and the other may have an infrared-centered wavelength.

The signals 103 may be transmitted through or reflected by the patient's tissue. In either case, the signals are modulated by the patient's blood to provide information regarding blood oxygen saturation in a manner that is well known. The transmitted signals 103 are received by the detector 110 which, in the illustrated embodiment, provides an analog current output signal 105 representative of the detected signals 103. This detector signal 105 is then processed by signal processing module 112. The processing module 112 may include a number of components that may be embodied in software, firmware and/or hardware. These components may include components for amplifying the signal 105 and converting the signal from a current signal to a voltage signal, filtering the signal to remove certain components of noise and otherwise conditioning the signal. In the illustrated embodiment, the signal processing module 112 also includes an analog to digital converter for converting the signal into a digital signal and a demultiplexer component for providing two separate output signals 118 or pleths that generally correspond to the two separate channel signals 103. These pleths 118 are then used by oxygenation calculation module 116 to compute a value related to blood oxygen saturation, e.g., a blood oxygen saturation percentage. A number of algorithms for performing such calculations are known and such calculation techniques are disclosed in U.S. Pat. No. 5,934,277 by Mortz and U.S. Pat. No. 5,842,979 by Jarmal, which are incorporated herein by reference.

The present invention involves monitoring effects related to the Mayer Wave such as low frequency blood volume and heart rate variability. An implementation for monitoring heart rate variability is discussed below followed by an implementation for monitoring blood volume variability. Both cases involve analysis of a pleth signal.

Figure 2:
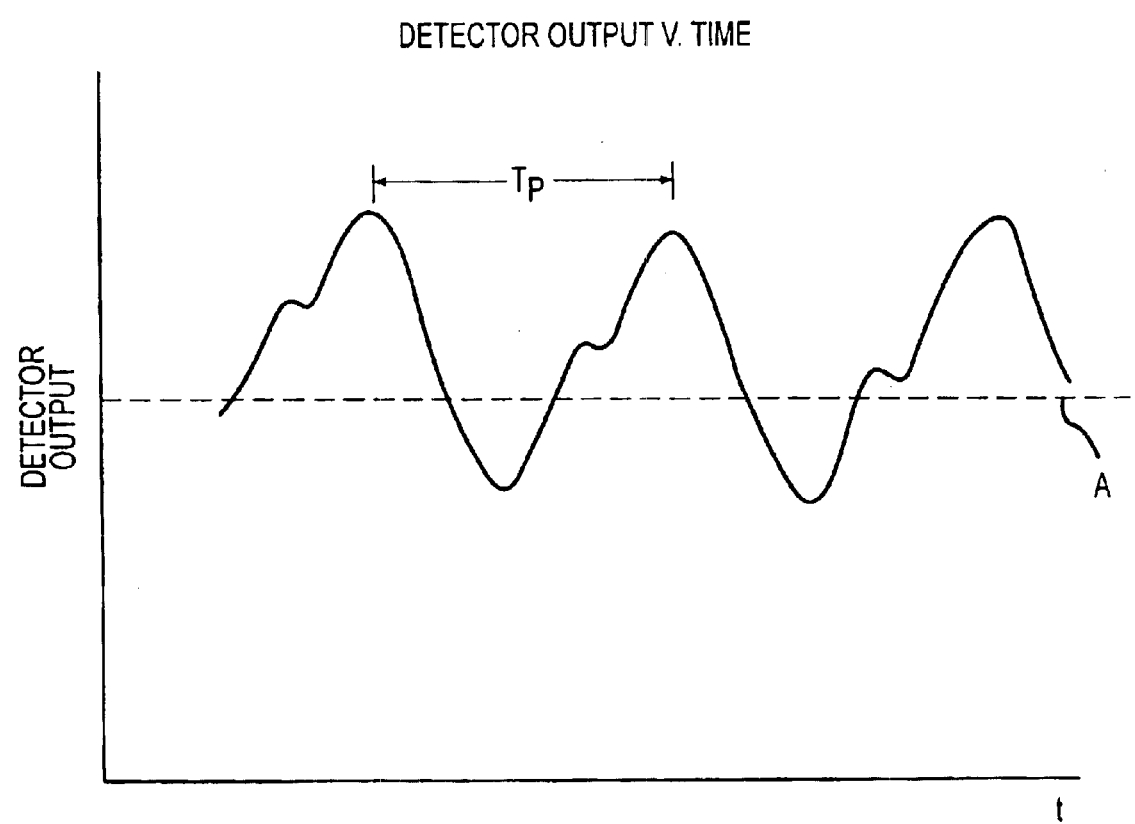
FIG. 2 illustrates the waveform of a pleth that may be used to obtain physiological parameter information in accordance with the present invention.

FIG. 2 illustrates an exemplary waveform of a pleth as such information may be obtained by the processor of a pulse oximeter. In particular, such information may be obtained as a digital signal output by the A/D converter, i.e., a time series of values related to the detector output. Such values are shown graphically in FIG. 2. As noted above, the pleth corresponding to either of the oximetry channels, or a combination of the channels, may be used in accordance with the present invention. It is desirable to obtain a strong pleth signal so that the waveform and pulse rate can be accurately identified. Accordingly, for normally oxygenated patients, the infrared channel pleth may be utilized. For poorly oxygenated patients, the red pleth may be preferred. In this regard, a cut off oxygenation level such as 85% may be used in determining whether to use the infrared or red pleth. Alternatively, the two pleth signals may be mathematically blended, depending on the current oxygenation level to obtain an optimized pleth for subsequent analysis in accordance with the present invention. Such selection or blending of the individual channel pleth signals is described in detail in U.S. patent application Ser. No. 09/975,289 by Hanna, which is incorporated herein by reference.

As shown in FIG. 2, the pleth signal includes a pulsatile component having a period designated $T_p$. This period corresponds to the patient's heart rate. The heart rate can be determined by monitoring this pleth in a variety of ways such as identifying a change in sign of a differential value of the waveform, tracking crossings of an average value indicated by A, or, as will be discussed in more detail below, by using a filter to track the fundamental frequency of the pleth.

Figure 3:
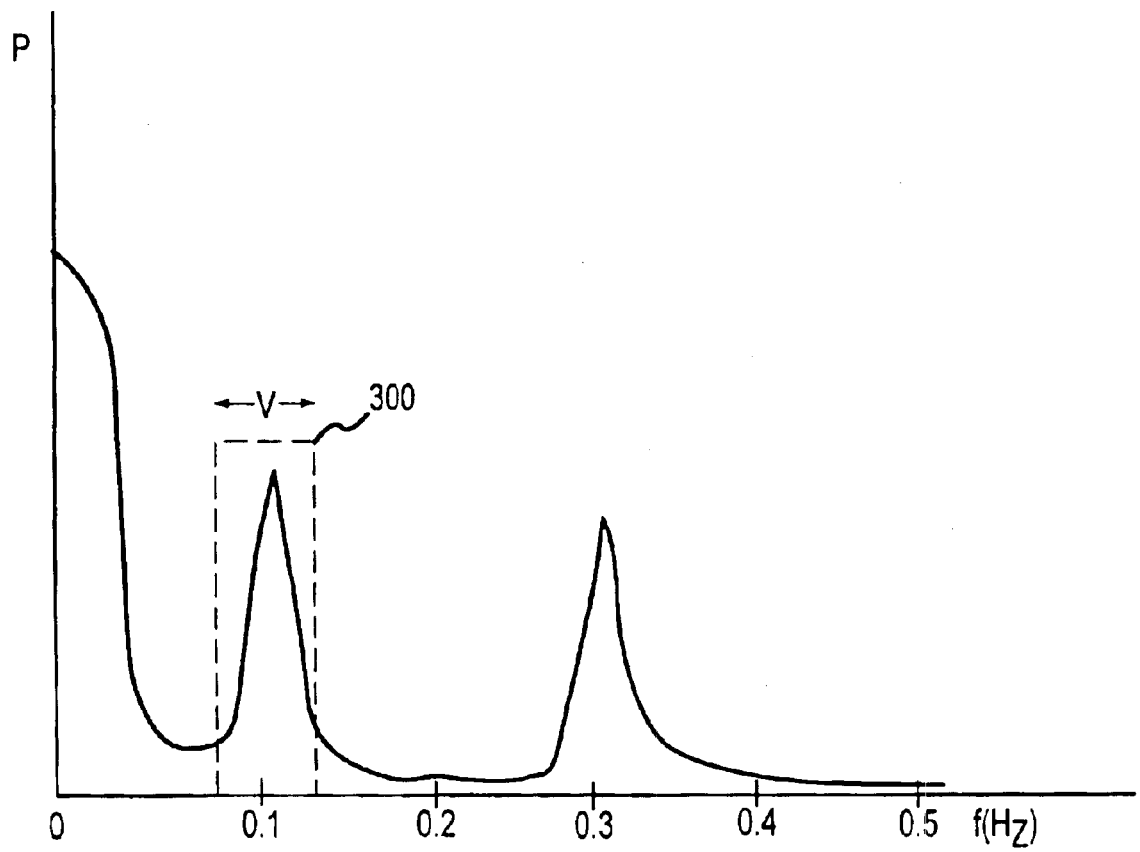
FIG. 3 is a graph illustrating the low frequency power spectrum of a pleth signal and a pass band of a filter used in accordance with the present invention.

In accordance with the present invention, the patient's respiration is monitored by tracking low frequency heart rate changes. FIG. 3 shows an exemplary pleth power spectrum. The spectrum is characterized by three discrete peaks. These include a peak typically around 0.3–0.5 Hz, a peak typically around 0.1 Hz and a peak below 0.05 Hz. The peak below 0.05 Hz is generally linked with vaso motor control and temperature control. The peak at around 0.1 Hz is generally associated with the Mayer Wave. As noted above, this phenomenon is not well understood but has been correlated to hypertension, sudden cardiac death, ventricular tachycardia, coronary artery disease, myocardial infarction, heart failure, diabetes, and autonomic neuropathy and has been seen to change after heart transplantation. The remaining peak, at about 0.3–0.5 Hz is believed to be correlated with respiration. This peak may have a significantly higher frequency for infants.

From the foregoing discussion, it will be appreciated that low frequency heart rate variability associated with the Mayer Wave can be monitored by: 1) determining heart rate based on an analysis of the pleth signal, 2) monitoring this heart rate over time to obtain a time series heart rate values, and 3) analyzing the time series heart rate values to identify a low frequency variability. These steps can be executed using adaptive filters as discussed below.

Figure 4:
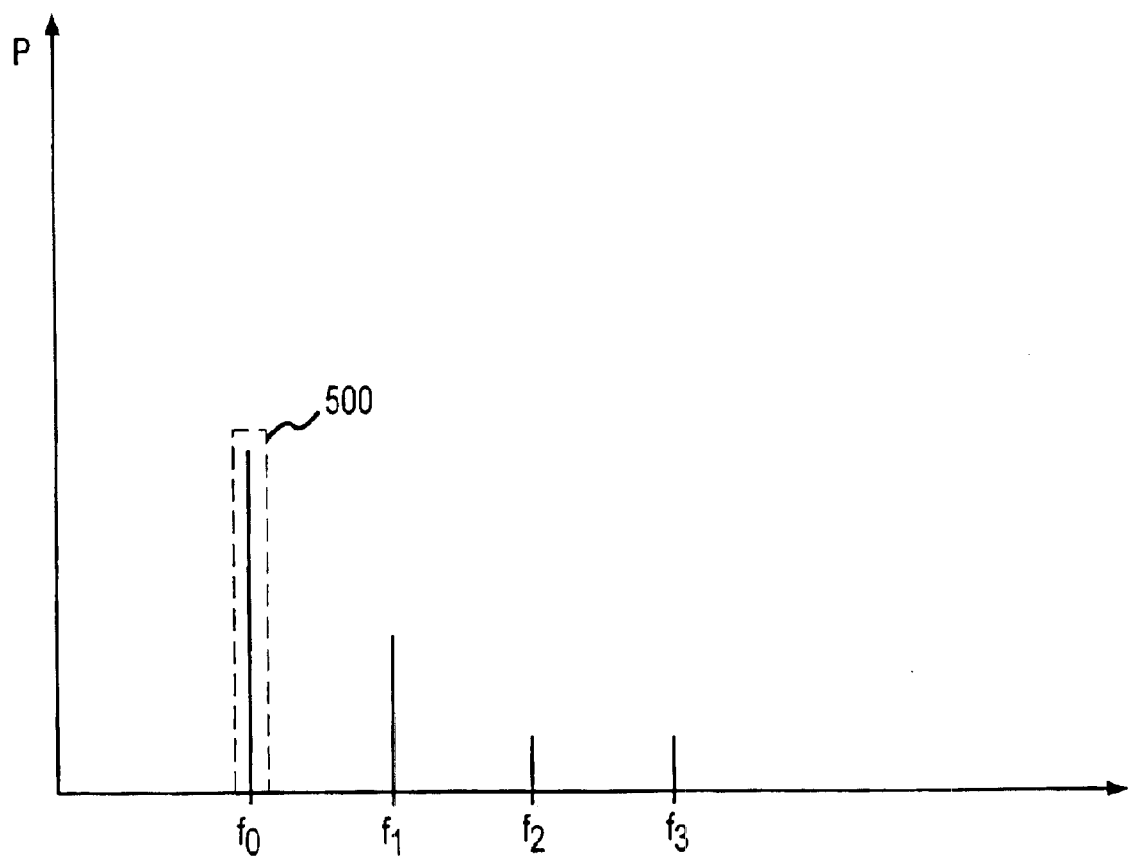
FIG. 4 is a chart illustrating a pleth signal power spectrum and a pass band of a filter used in accordance with the present invention.

FIG. 4 illustrates a pleth power spectrum. Such a power spectrum may be obtained by configuring the oximeter processor to mathematically obtain a Fourier transform of the time domain pleth signal. As shown, the pleth power spectrum has a fundamental frequency at to corresponding to the patient's heart rate. Additional peaks of the illustrated power spectrum relate to harmonics thereof. The present invention utilizes an adaptive filter adapted to function as a band pass filter having a narrow band pass encompassing the fundamental frequency. The transfer function of this filter is generally indicated by function 500. A variety of different types of filters may be used in this regard. Generally, such filters track the fundamental frequency of a signal based on certain programmed information regarding the nature of the signal as well as by monitoring successive signal waveforms. Such filters are robust in operation and can provide a continually updated output, in this case, regarding pulse rate. Thus, such a filter can provide as an output a time series of pulse rates of values or pulse rate signal.

An additional digital filter can be used to extract from this pulse rate signal a low frequency variation therein associated with the Mayer Wave. Referring again to FIG. 3, the Mayer Wave has a frequency around 0.1 Hz. Accordingly, the low frequency variation in pulse rate associated with the Mayer Wave can be extracted from the pulse rate signal by filtering the pulse rate signal using a band pass filter having a pass band encompassing the Mayer Wave frequency. The transfer function of such a band pass filter is graphically illustrated by function 300 of FIG. 3. This band pass has a width, w, and a center frequency selected to pass the Mayer Wave components and substantially exclude interference from the very low frequency peak and the peak associated with the respiration wave as discussed above. On the other hand, the width, w, should be sufficient to accommodate small variations in Mayer Wave frequency which are of interest for diagnostic purposes. Accordingly, the lower end of the pass band is preferably at least 0.05 Hz. As noted above, the upper end of the pass band can be selected in conjunction with the patient's respiration rate which may be controlled. Thus, the upper end of the pass band is preferably no greater than about 0.5 Hz or 1.5 Hz to accommodate neonatal applications and, more preferably, is no greater than about 0.3 Hz. In the illustrated embodiment, the band pass filter has a lower limit of about 0.08 Hz and an upper limit of about 0.4 Hz. Alternatively, an adaptive filter may be used to track the Mayer Wave component. In particular, such an adaptive filter may function as a band pass filter having a transfer function that can shift to track the frequency of the Mayer Wave component.

Figure 5:
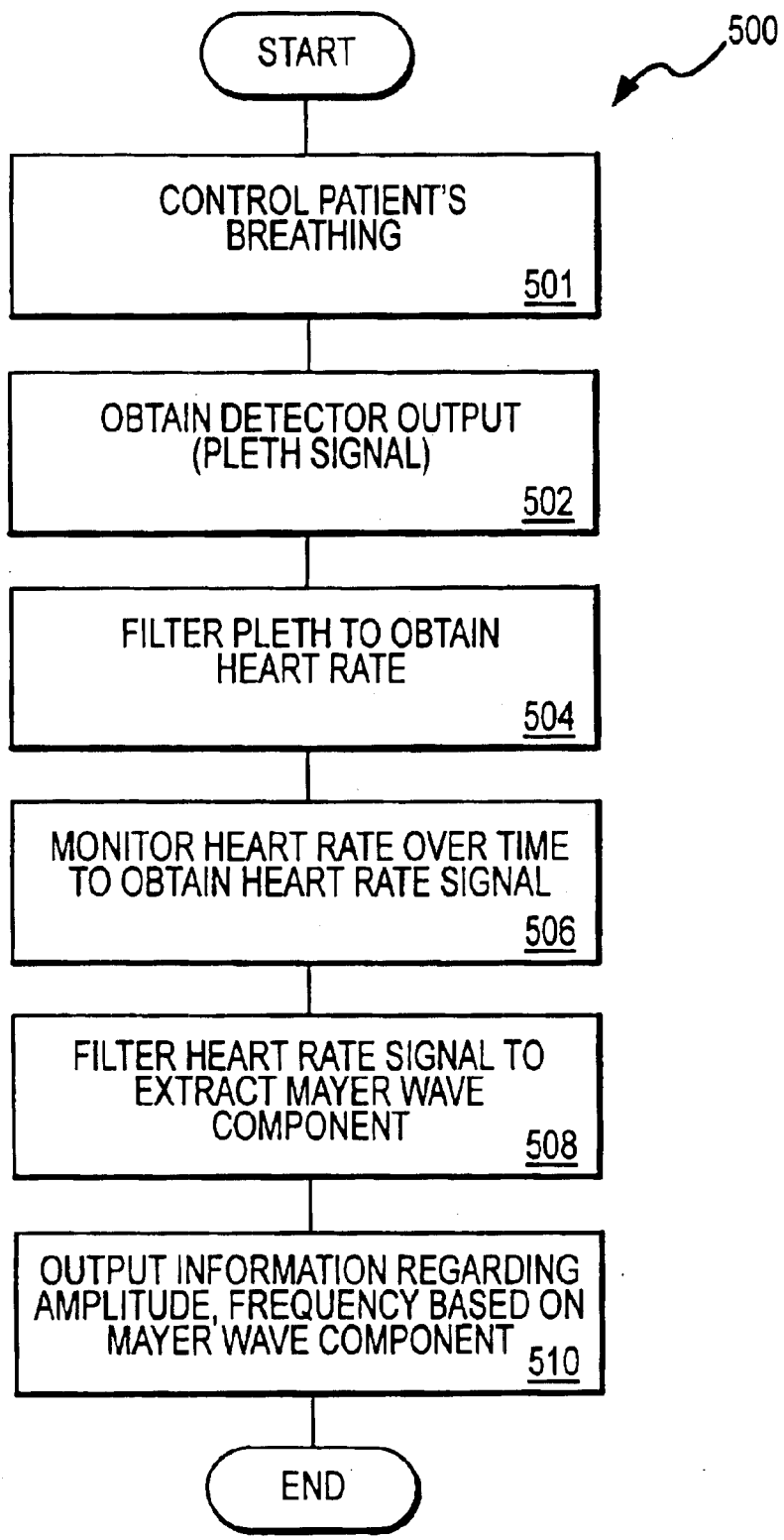
FIG. 5 is a flow chart illustrating a process for monitoring a Mayer Wave effect based on a photoplethysmographic heart rate signal in accordance with the present invention.

FIG. 5 is a flow chart illustrating a process for monitoring low frequency variations in heart rate based on pleth signals in accordance with the present invention. The process 500 is initiated by controlling (501) the patient's breathing to be at a frequency of at least a predetermined threshold and obtaining (502) a detector output or pleth signal. The patient's breathing may be controlled by instructing the patient to breath at the desired rate or by using a respirator. The threshold may be selected based on the pass band of the filter as discussed above. In the context of a pulse oximeter, obtaining the pleth signal may involve receiving the digital output from an A/D converter that reflects the detector signal, demodulating this signal to obtain individual channel components and selecting a pleth for further processing. The selected pleth may be one of the channels or an optimized pleth signal based on both of the channel components. The pleth is then filtered (504), e.g., using an adaptive filter to track the fundamental frequency of the pleth signal, to obtain a time series of heart rate values. These values are monitored (506) over time to obtain a heart rate signal. The heart rate signal is then filtered (508) using a band pass filter or adaptive filter as discussed above to extract a frequency component related to the Mayer Wave. Information regarding this frequency component is then output (510), e.g., as a graphical waveform display or as numerical values. Preferably, this information relates to an amplitude, frequency or variation therein based on the extracted Mayer Wave component. This information may be displayed in the display area of a conventional pulse oximeter programmed to provide such information.

Figure 6:
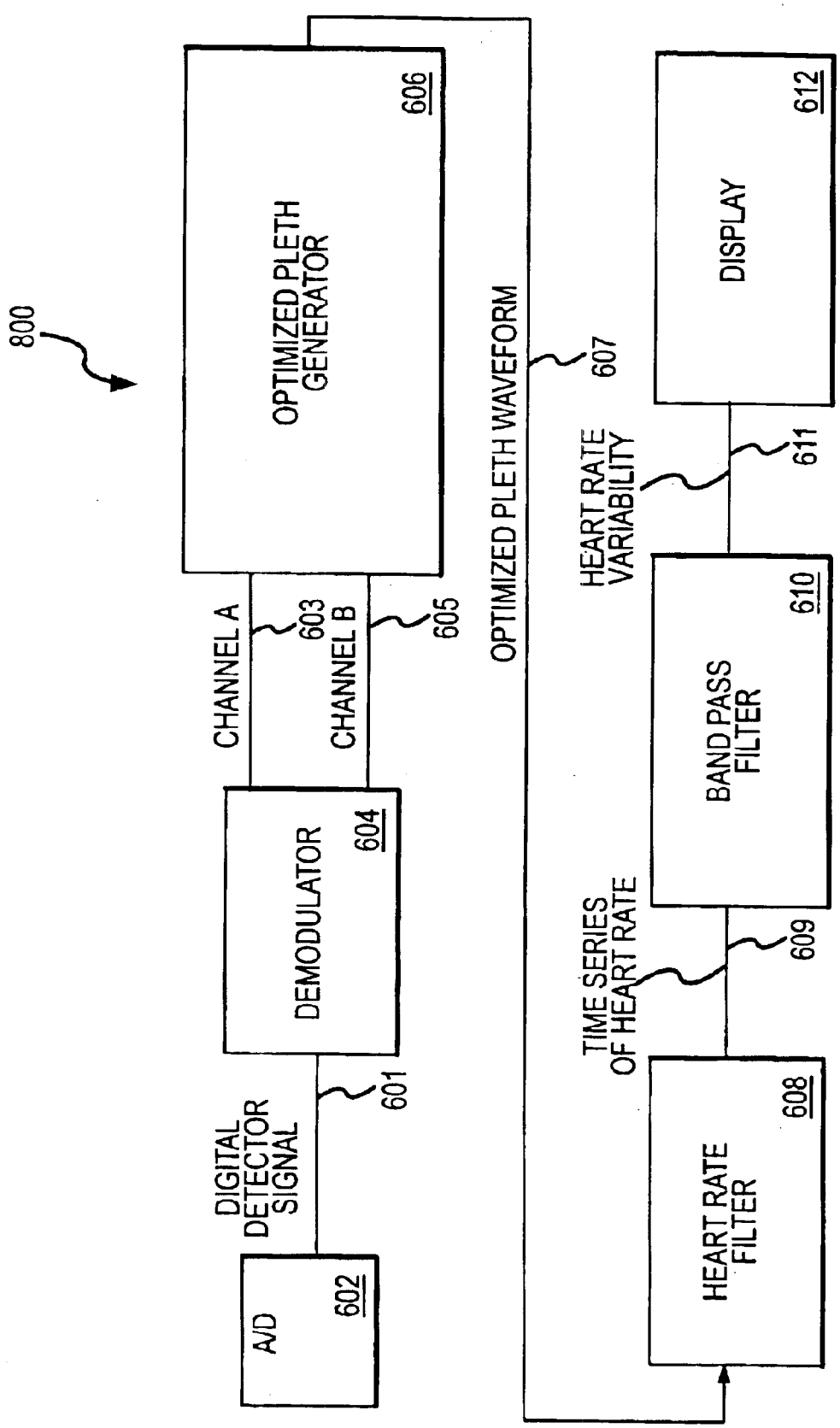
FIG. 6 is a schematic diagram of a pulse oximetry system adapted for monitoring a Mayer Wave effect based on a photoplethysmographic heart rate signal.

The corresponding components of a pulse oximeter processing unit are illustrated in FIG. 6. The illustrative unit 600 includes an A/D converter 602. The A/D converter 602 receives an analog signal representative of the optical signal received by the pulse oximeter detector. This analog input signal is processed by the converter (602) to provide a digital detector signal 603. The digital detector signal 603 is then processed by demodulator 604 to provide two separate channel signals designated channel A (605) and channel B (607), that may correspond, for example, to the red and infrared channels of the pulse oximeter. These channel signals are then processed in the illustrated embodiment by the optimized pleth generator 606 to provide an optimized pleth waveform 609. As discussed above, the optimized pleth waveform may correspond to either of the channel signals or a combination thereof. This optimized waveform 609 is processed by a heart rate filter in order to track the fundamental frequency of the waveform which corresponds to the patient's heart rate. The output from the heart rate filter 608 is a time series of heart rate values 611. This time series heart rate values is then processed by a band pass filter 610 which passes the Mayer Wave component of the corresponding spectrum to identify the associated low frequency heart rate variability. Associated information 613 may be periodically output to a user via a display 612.

FIGS. 7–17 relate to monitoring an alternative Mayer Wave effect; namely, low frequency blood volume variability. As noted above, the Mayer Wave is associated with a number of effects including low frequency variability in heart rate, blood volume, blood pressure and vasoconstriction. It will be appreciated that variations in blood volume can be directly monitored from the pleth signal. In particular, the attenuation of optical signals in a pulse oximeter is proportional to the effective optical path length which in turn is related to blood volume. A number of factors affect blood volume including, notably, the patient's pulse. Thus, the pleth signal will include a component having a pulsatile waveform. This pulsatile waveform is effectively modulated by the Mayer Wave. Thus, if potentially interfering effects such as patient respiration are accounted for, the Mayer Wave component can be extracted from the pleth signal by band pass filtering using a band pass filter or adaptive filter as discussed above in connection with FIG. 3 (in this case used to filter the pleth signal rather than a heart rate signal). The patient's breathing can be controlled to have a frequency outside of the pass band of this filter. In particular, when possible, the patient can be instructed to breathe at a frequency of at least 0.167 Hz (10 breaths per minute) and, more preferably, at least about 0.333 Hz (20 breaths per minute). Alternatively, the patient's breathing can be controlled in this regard using a respirator.

Figure 7:
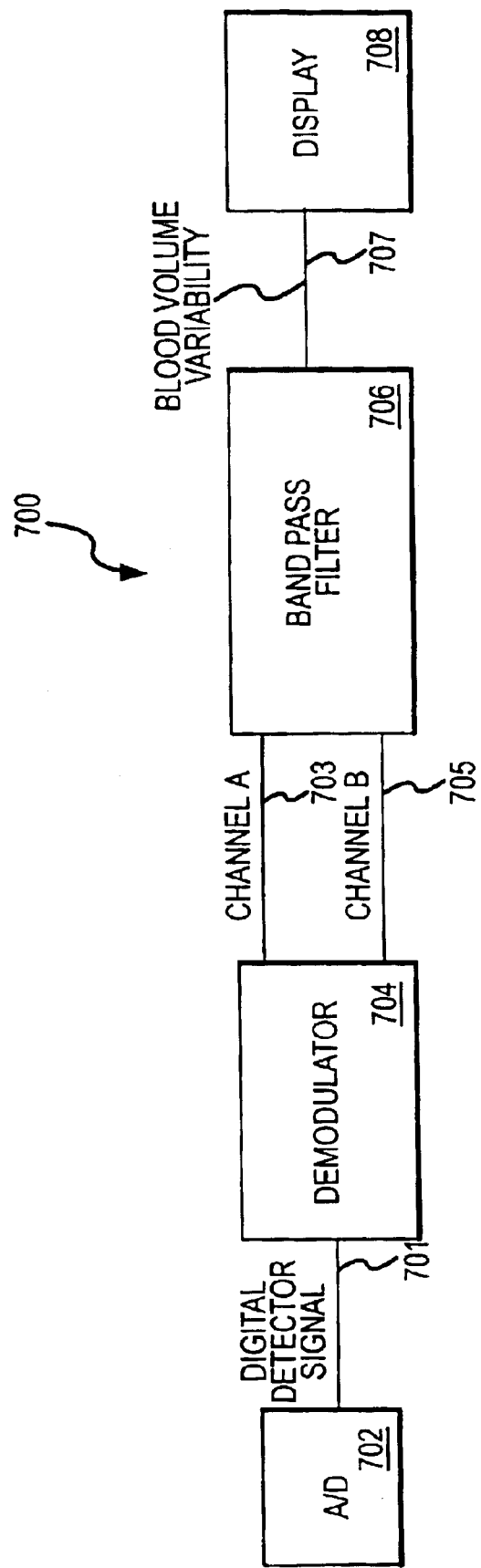
FIG. 7 is a schematic diagram of a pulse oximetry system adapted for monitoring low frequency blood volume variability in accordance with the present invention.

The corresponding components of a pulse oximeter processing unit are illustrated in FIG. 7. The illustrated unit 700 includes and A/D converter 702. The A/D converter functions as described above in connection with FIG. 6 to receive an analog signal representative of the optical signal received by the pulse oximeter detector and provide a corresponding digital detector signal 701. The digital detector signal 701 is then processed by a demodulator 704 to provide two separate channel signals designated channel A (703) and channel B (705), that may correspond, for example, to the red and infrared channels of the pulse oximeter. The pleth signal corresponding to either one of these channels or a combined signal based on both channels is then filtered by band pass filter 706 as described above to extract a component 707 related to blood volume variability. Information related to blood volume variability is then provided via the display 708. Such information may include a waveform of the blood volume variability signal, a frequency or amplitude of the blood volume variability waveform and/or a value related to a variation of the amplitude or frequency.

Figure 8:
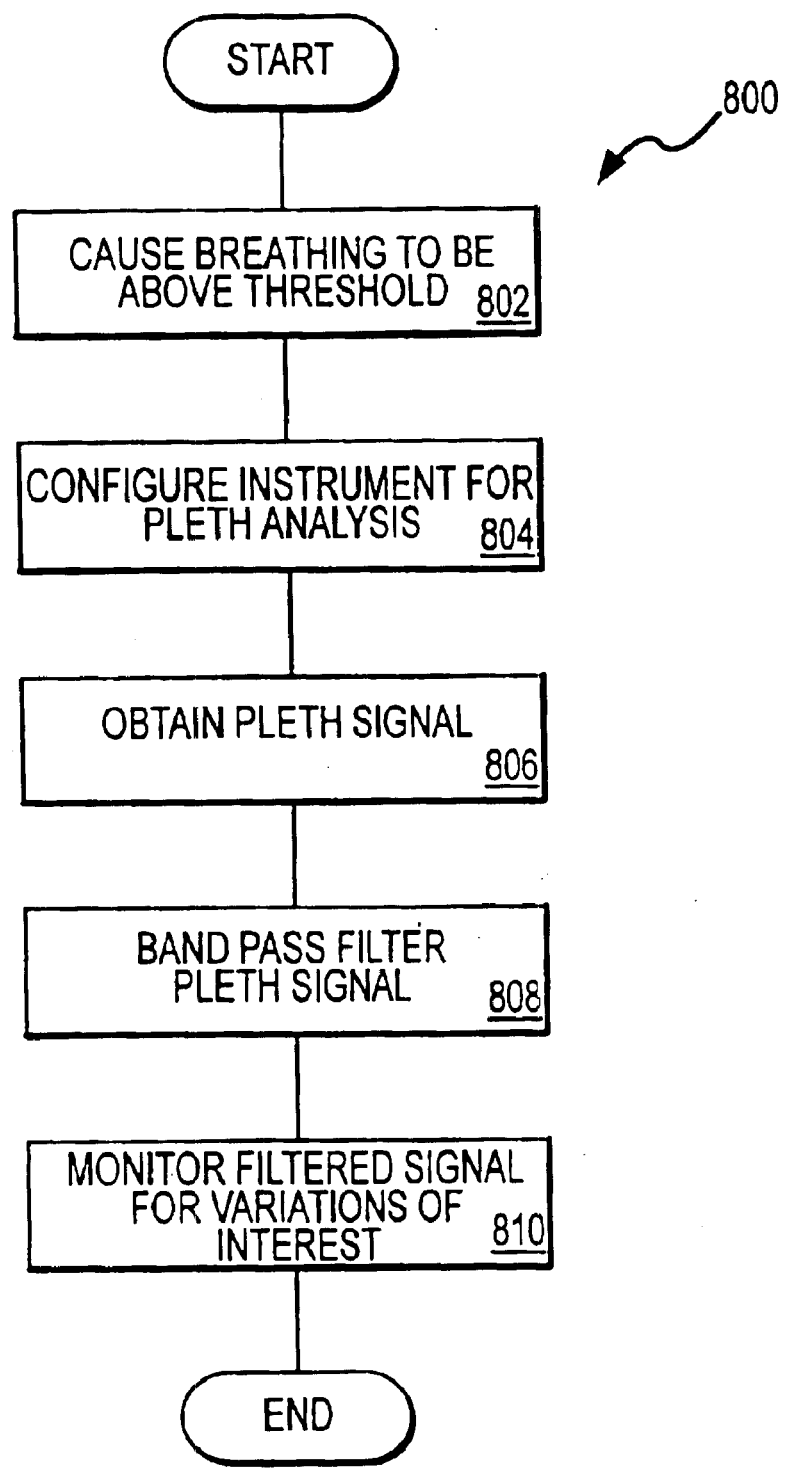
FIG. 8 is a flow chart illustrating a process for monitoring low frequency blood volume variability in accordance with the present invention.

FIG. 8 is flow chart illustrating a process 800 for monitoring blood volume variability. The process 800 is initiated by causing (802) a patient's breathing rate to be above a selected threshold. As discussed above, when possible, the patient may be instructed to control his breathing. Alternatively, the patient's breathing may be artificially controlled. For example, the patient's breathing rate may be controlled to be at least about 10 breaths per minute and more preferably at least about 20 breaths per minute. The pulse oximetry instrument is then configured (804) to obtain a pleth signal, e.g., by placing a probe on the patient's finger, and the instrument is operated to obtain (806) a pleth signal. This pleth signal, which may correspond to one or more of the oximeter channels, is then band pass filtered (808) to extract a low frequency blood volume variability component associated with the Mayer Wave. The filtered signals are monitored (810) to identify any variations of interest. In this regard, variations in the amplitude or frequency of the Mayer Wave may be of diagnostic significance.

Figure 9:
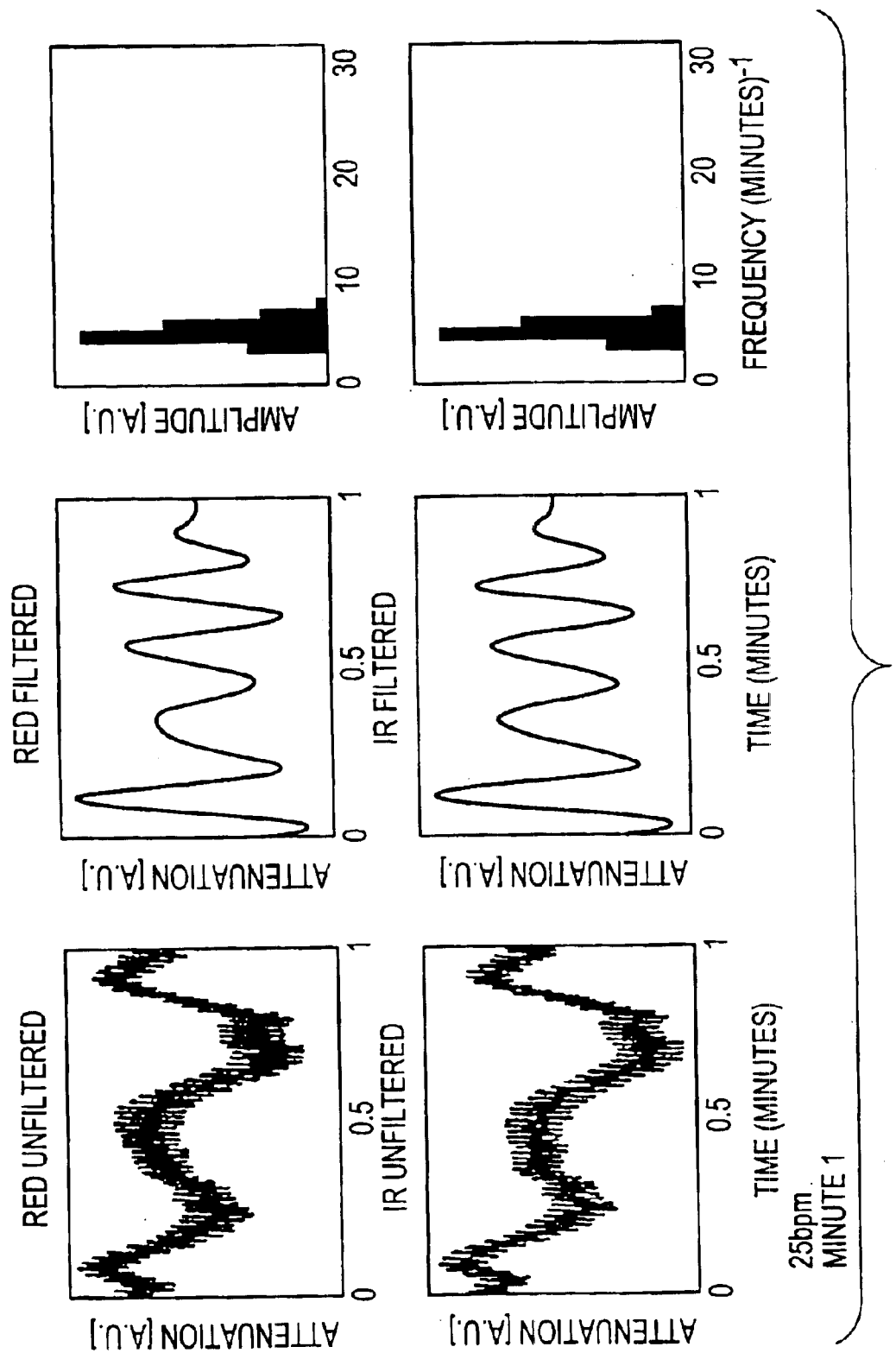
FIGS. 9–16 show the results of various procedures performed to monitor Mayer Wave effects in accordance with the present invention.
Figure 10:
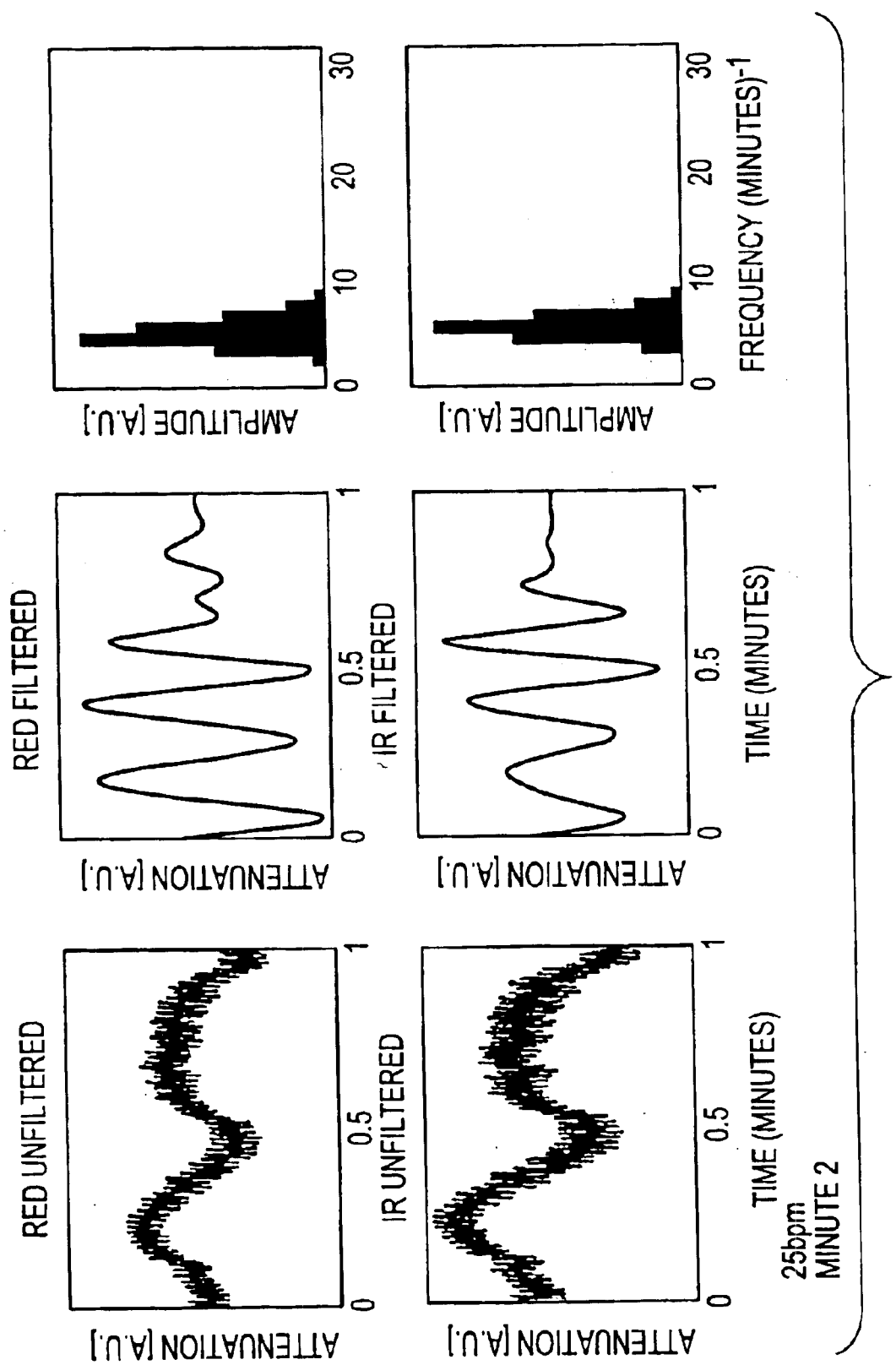
Figure 11:
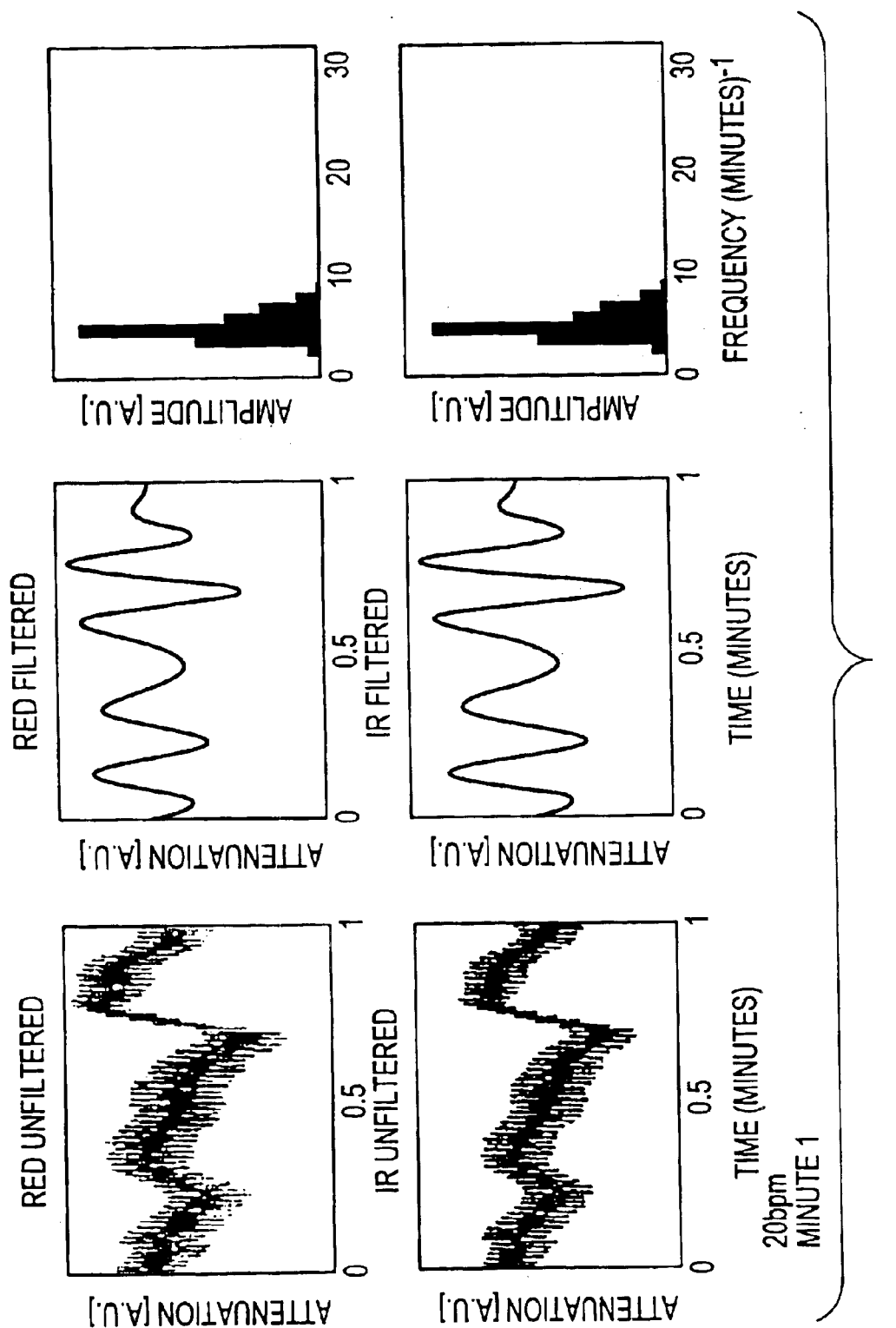
Figure 12:
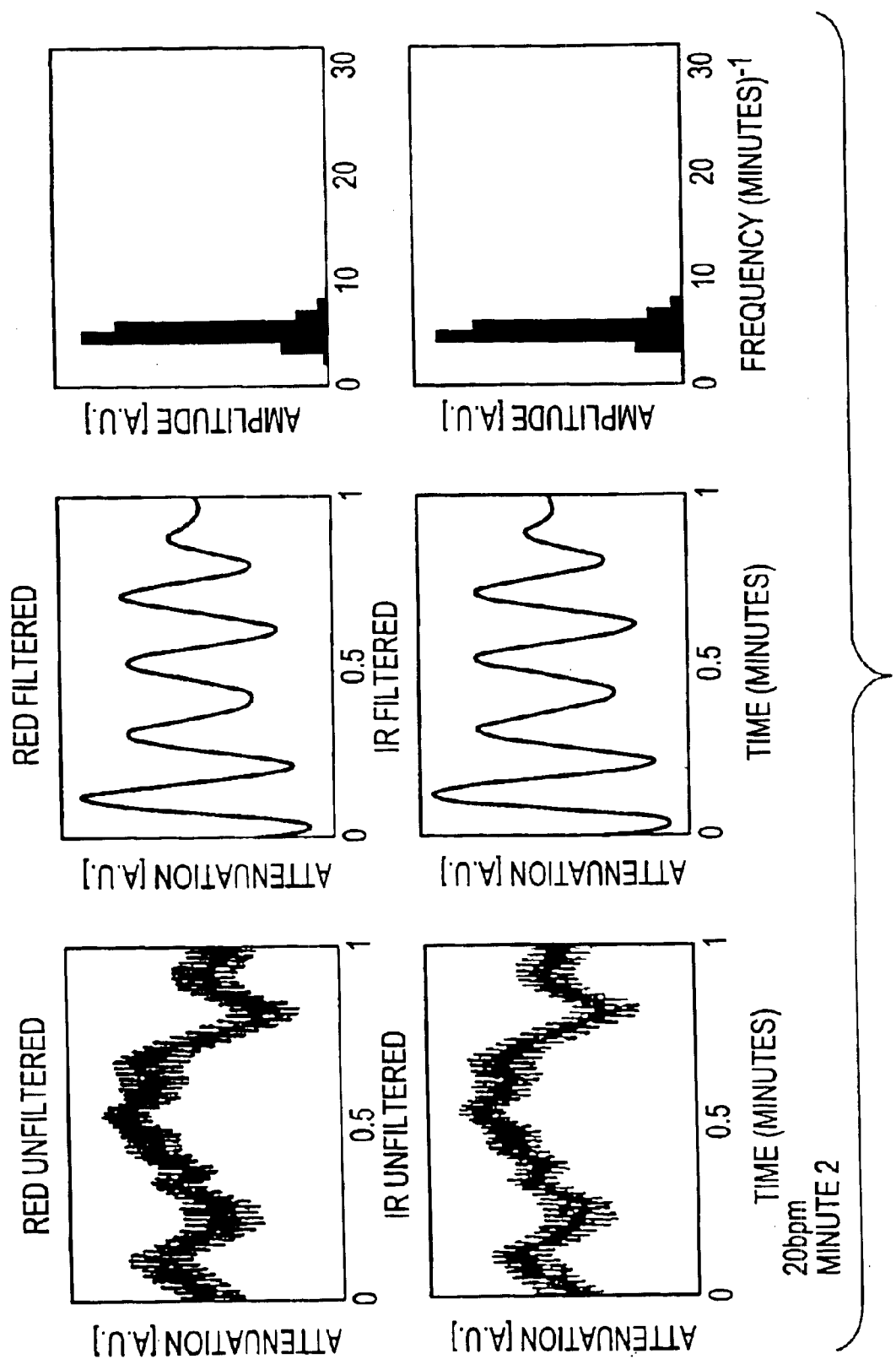
Figure 13:
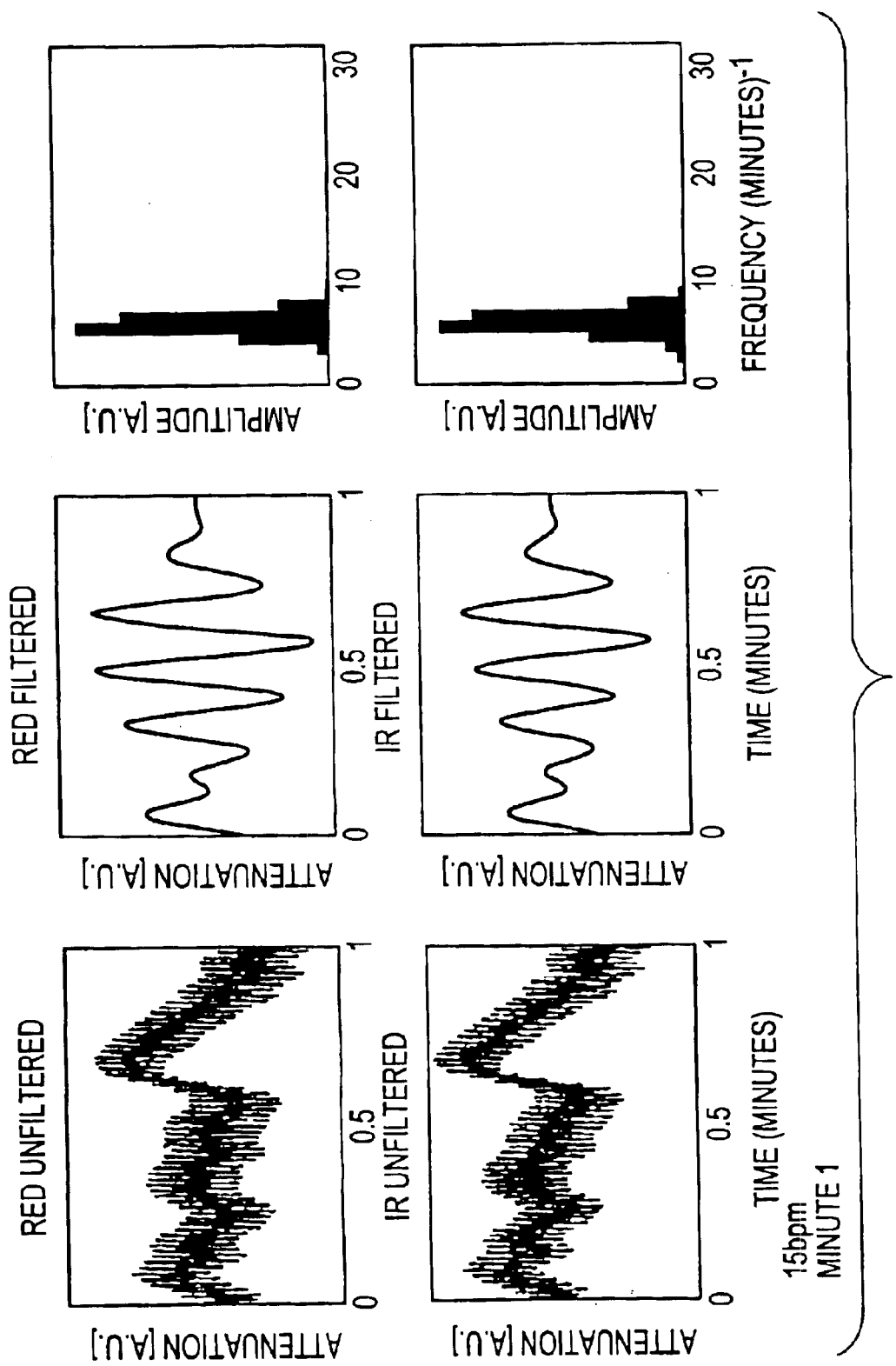
Figure 14:
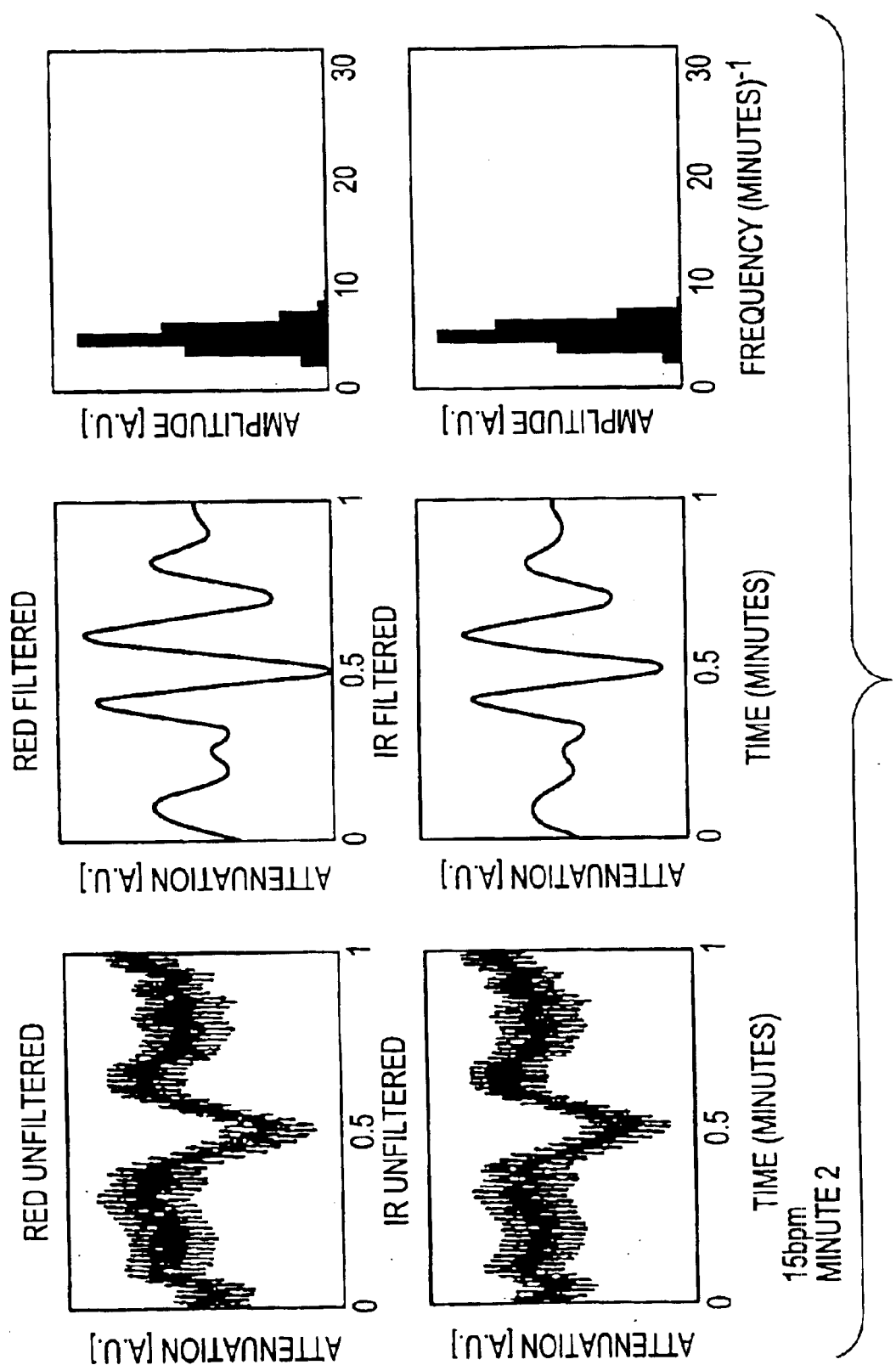
Figure 15:
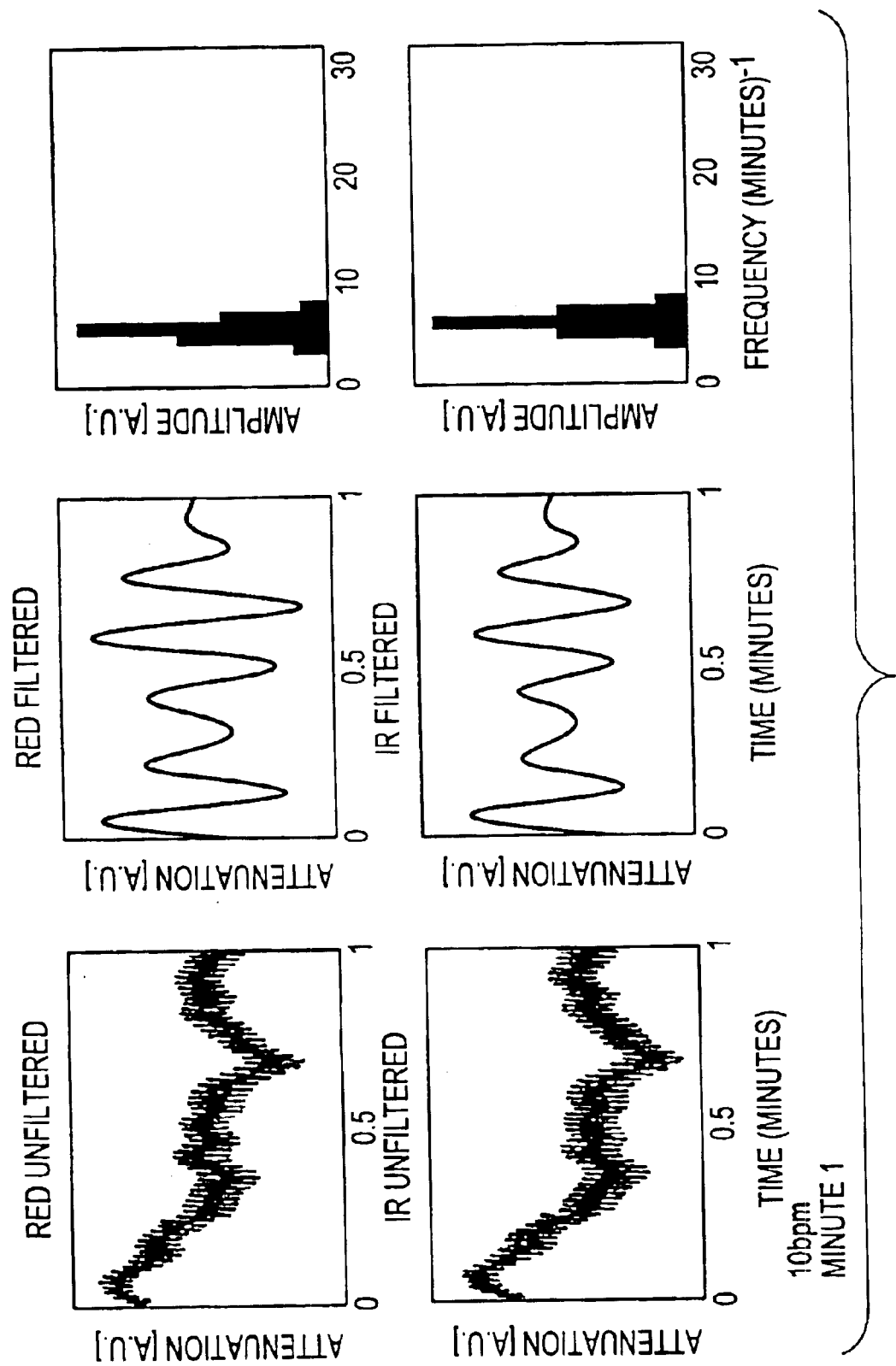
Figure 16:
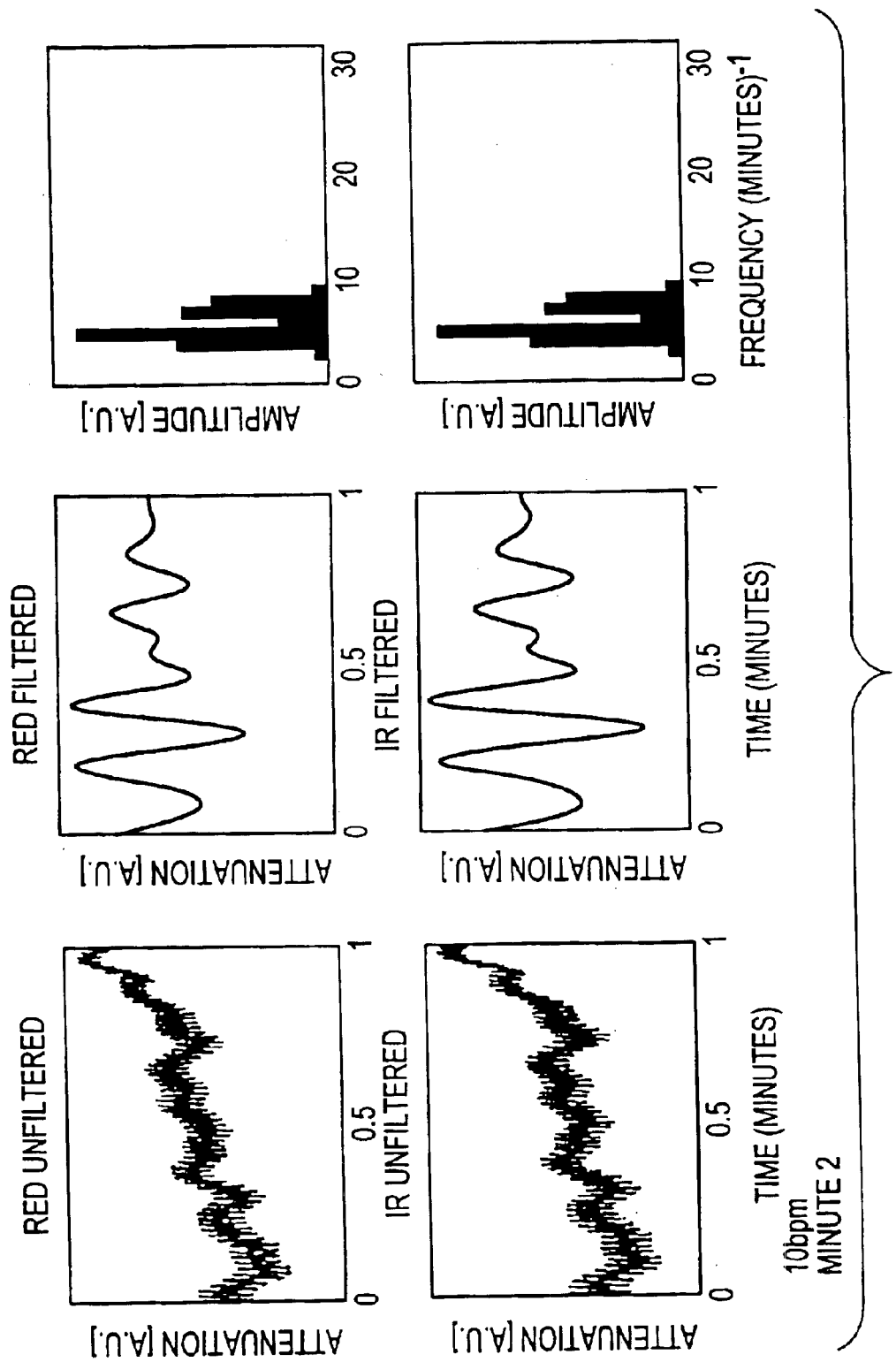

FIGS. 9–16 illustrate the results of procedures performed in accordance with the present invention. In particular, four two minute measurements were conducted on a subject breathing at 25, 20, 15 and 10 breaths per minute. FIG. 9 illustrates the results for the first minute at 25 breaths per minute, FIG. 10 shows the results for the second minute at a breathing rate of 25 breaths per minute, FIG. 11 shows the results for the first minute at 20 breaths per minute, FIG. 12 shows the results for the second minute at 20 breaths per minute, FIG. 13 shows the results for the first minute at 15 breaths per minute, FIG. 14 shows the results for the second minute at 15 breaths per minute, FIG. 15 shows the results for the first minute at 10 breaths per minute and FIG. 16 shows the results for the second minute at 10 breaths per minute. Each of these Figures includes top and bottom rows of panels corresponding to the red and infrared channels, respectively, of the pulse oximeter detector signal. Each row includes a first panel that shows the unfiltered pleth signal, a second panel that shows the pleth signal after filtering to extract the Mayer Wave related component of blood volume variability and the final panel shows the resulting spectrum of the low frequency blood volume variability related to the Mayer Wave. As shown, the amplitude and frequency of the Mayer Wave related components are clearly visible in each of the test results, thus allowing for monitoring of a Mayer Wave effect of potential diagnostic significance.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for use in monitoring a patient, comprising the steps of:
    configuring a photoplethysmographic ("pleth") instrument relative to a patient for a pleth analysis;
    causing a respiration rate of said patient to be at least at a given threshold, wherein a frequency of said respiration rate is elevated above a frequency range associated with a Mayer Wave;
    first operating said pleth instrument to obtain a pleth signal for said patient; and
    second operating said pleth instrument to process said pleth signal for identifying an effect related to said Mayer Wave and providing an output related to said Mayer Wave effect.

2. A method as set forth in claim 1, wherein said step of configuring comprises applying a probe of said instrument to said patient so as to transmit an optical signal to perfused tissue of said patient.

3. A method as set forth in claim 1, wherein said step of causing comprises instructing said patient to breathe at at least a predetermined threshold.

4. A method as set forth in claim 3, wherein said predetermined threshold is at least 10 breaths per minute.

5. A method as set forth in claim 3, wherein said predetermined threshold is at least 20 breaths per minute.

6. A method as set forth in claim 1, wherein said step of causing comprises controlling said patient's respiration rate with a respirator.

7. A method as set forth in claim 1, wherein said step of second operating comprises causing said instrument to process said pleth signal to obtain heart rate information and process said heart rate information to obtain information regarding heart rate variability.

8. A method as set forth in claim 1, wherein said step of second operating comprises causing said instrument to process said pleth signal to obtain information regarding a low frequency blood volume variation of said patient.

* * * * *